United States Patent [19]
Scirica

[11] Patent Number: 5,980,569
[45] Date of Patent: Nov. 9, 1999

[54] PROSTHETIC VALVE HOLDER AND METHOD OF USE

[75] Inventor: Paul A. Scirica, Huntington, Conn.

[73] Assignee: United States Surgical Corp., Norwalk, Conn.

[21] Appl. No.: 08/934,110

[22] Filed: Sep. 19, 1997

[51] Int. Cl.⁶ .................................................. A61F 2/24
[52] U.S. Cl. ................................................................ 623/2
[58] Field of Search .......................... 623/900, 2; 606/1; 24/517

[56] References Cited

U.S. PATENT DOCUMENTS

| | | |
|---|---|---|
| Re. 34,150 | 12/1992 | Santilli et al. . |
| 497,064 | 5/1893 | Van Meter . |
| 1,157,202 | 10/1915 | Bates et al. . |
| 1,400,616 | 12/1921 | McCrory et al. . |
| 1,453,863 | 5/1923 | Conard ..................................... 24/517 |
| 1,707,689 | 4/1929 | Sloan . |
| 1,839,726 | 1/1932 | Arnold . |
| 1,919,120 | 7/1933 | O'Connor et al. . |
| 1,963,173 | 6/1934 | Morin . |
| 2,053,868 | 9/1936 | Grosso . |
| 2,384,304 | 9/1945 | Helfrick . |
| 2,460,470 | 2/1949 | Rogers ..................................... 24/517 |
| 2,473,266 | 6/1949 | Wexler . |
| 2,623,517 | 12/1952 | Barlow et al. . |
| 2,701,562 | 2/1955 | Michale et al. . |
| 3,070,088 | 12/1962 | Brahos . |
| 3,129,706 | 4/1964 | Reynolds, Jr. . |
| 3,168,093 | 2/1965 | Gauthier . |
| 3,384,077 | 5/1968 | Gauthier . |
| 3,409,013 | 11/1968 | Berry ......................................... 606/1 |
| 3,463,744 | 8/1969 | Hammond . |
| 3,509,873 | 5/1970 | Karlin et al. . |
| 3,522,799 | 8/1970 | Gauthier . |
| 3,587,115 | 6/1971 | Shiley . |
| 3,724,449 | 4/1973 | Gauthier . |
| 3,828,787 | 8/1974 | Anderson et al. . |
| 3,858,578 | 1/1975 | Milo . |
| 3,965,890 | 6/1976 | Gauthier . |
| 3,998,217 | 12/1976 | Trumbull et al. . |
| 4,010,741 | 3/1977 | Gauthier . |
| 4,048,987 | 9/1977 | Hurson . |
| 4,190,042 | 2/1980 | Sinnreich . |
| 4,254,763 | 3/1981 | McCready et al. . |
| 4,337,762 | 7/1982 | Gauthier . |
| 4,421,107 | 12/1983 | Estes et al. . |
| 4,424,724 | 1/1984 | Bookwalter et al. . |
| 4,430,991 | 2/1984 | Darnell . |
| 4,457,300 | 7/1984 | Budde . |
| 4,562,832 | 1/1986 | Wilder et al. . |
| 4,585,453 | 4/1986 | Martin et al. . |
| 4,627,421 | 12/1986 | Symbas et al. . |
| 4,655,218 | 4/1987 | Kulik et al. ................................. 623/2 |

(List continued on next page.)

FOREIGN PATENT DOCUMENTS

| | | |
|---|---|---|
| 0246086 | 11/1987 | European Pat. Off. . |
| 1005345 | 12/1951 | France . |
| 1008937 | 7/1984 | U.S.S.R. ..................................... 623/2 |
| 1621912 | 1/1991 | U.S.S.R. ..................................... 623/2 |
| 2102681 | 2/1983 | United Kingdom . |
| 8904145 | 5/1989 | WIPO . |
| 92012688 | 8/1992 | WIPO ..................................... 623/900 |
| 9221296 | 12/1992 | WIPO . |
| 95017139 | 6/1995 | WIPO ..................................... 623/2 |

*Primary Examiner*—Gene Mancene
*Assistant Examiner*—Eduardo C. Robert

[57] ABSTRACT

A prosthetic valve holder includes a first end portion for rigidly mounting to an articulating arm. A second end portion has two opposing tines for capturing a valve used for valve replacement surgery. By securing a prosthetic valve to the valve holder, the valve can be positioned for installation. Finally, the valve holder is detached from the valve. Various alternate embodiments of the valve holder are provided. A method of surgery using the valve holder is also provided and includes providing an articulating arm having a distal-most end. After attaching a prosthetic valve to a valve holder, a valve is installed and detached from the holder.

4 Claims, 7 Drawing Sheets

U.S. PATENT DOCUMENTS

| | | |
|---|---|---|
| 4,683,883 | 8/1987 | Martin . |
| 4,700,230 | 10/1987 | Pshtissky et al. . |
| 4,726,356 | 2/1988 | Santilli et al. . |
| 4,744,363 | 5/1988 | Hasson . |
| 4,747,395 | 5/1988 | Brief . |
| 4,765,311 | 8/1988 | Kulik et al. . |
| 4,796,846 | 1/1989 | Meier et al. . |
| 4,813,401 | 3/1989 | Grieshaber . |
| 4,829,985 | 5/1989 | Couetil . |
| 4,852,552 | 8/1989 | Chaux . |
| 4,865,019 | 9/1989 | Phillips . |
| 4,865,600 | 9/1989 | Carpentier et al. . |
| 4,932,395 | 6/1990 | Mehdizadeh . |
| 4,949,707 | 8/1990 | LeVahn et al. . |
| 5,000,163 | 3/1991 | Ray et al. . |
| 5,025,779 | 6/1991 | Bugge . |
| 5,052,373 | 10/1991 | Michelson . |
| 5,052,374 | 10/1991 | Alvarez-Jacinto . |
| 5,067,477 | 11/1991 | Santangelo . |
| 5,074,858 | 12/1991 | Martinez . |
| 5,088,472 | 2/1992 | Fakhrai . |
| 5,167,223 | 12/1992 | Koros et al. . |
| 5,197,979 | 3/1993 | Quintero et al. ............................. 623/2 |
| 5,231,974 | 8/1993 | Giglio et al. . |
| 5,284,130 | 2/1994 | Ratliff . |
| 5,299,563 | 4/1994 | Seton . |
| 5,306,234 | 4/1994 | Johnson . |
| 5,370,685 | 12/1994 | Stevens . |
| 5,375,481 | 12/1994 | Cabrera et al. . |
| 5,400,774 | 3/1995 | Villalta et al. . |
| 5,476,510 | 12/1995 | Eberhardt et al. ...................... 623/900 |
| 5,480,425 | 1/1996 | Ogilive . |
| 5,503,617 | 4/1996 | Jako . |
| 5,520,610 | 5/1996 | Giglio et al. . |
| 5,531,785 | 7/1996 | Love et al. ............................. 623/900 |
| 5,545,214 | 8/1996 | Stevens . |
| 5,578,076 | 11/1996 | Krueger et al. . |
| 5,582,607 | 12/1996 | Lackman ...................... 606/1 |

PROSTHETIC VALVE HOLDER AND METHOD OF USE

BACKGROUND

1. Technical Field

The subject disclosure relates to minimally invasive surgical procedures and apparatus and, more particularly, to instruments and methods for performing heart valve replacement surgery.

2. Background

The diagnosis and treatment of coronary disease and related conditions often requires repair or replacement of the valves located within the heart. Various factors, such as, for example, calcification, may result in the mitral or aortic valves becoming impaired or functionally inoperative requiring replacement. Where replacement of a heart valve is indicated, in general, the dysfunctional valve is cut out and replaced with either an artificial, synthetic heart valve or a harvested porcine heart valve. The replacement valve is typically sutured in place of the original valve.

More specifically, access to the heart in a patient's thoracic cavity is achieved by making a longitudinal incision in the chest. This procedure, referred to as a median sternotomy includes cutting through the sternum and forcing the two opposing halves of the rib cage to be spread apart allowing access to the thoracic cavity and thus the heart.

Suitable instruments for spreading and holding apart the rib cage are marketed by United States Surgical Corporation, Norwalk, Conn. These instruments include, for example, Mini-CABG* retractors and relted accessories. The Mini-CABG* universal base retractor includes a substantially planar base having an opening which can be positioned on the patient such that the opening overlies the incision at the operative site. Mini-CABG* retractors are slidably mounted on the base and are provided to spread apart the rib cage halves and engage and retract obstructing tissue. Surgical instruments that can be used to stabilize or manipulate the heart during surgery can also be secured to the base.

Once access to the thoracic cavity has been achieved, surgery on the heart to effect valve replacement may be performed. During some procedures, the heart beat is arrested by infusion of a cardioplegic fluid, such as potassium chloride (KCl), to paralyze the myocardium while blood flow circulation is maintained through known heart bypass techniques. Alternatively, the heart is allowed to beat to maintain circulation, while a localized area of the heart on which surgery is to be performed, is locally immobilized by various instruments.

The heart is incised and the defective valve is cut away leaving a surrounding area of locally tougher tissue. Known heart valve replacement techniques typically include individually passing sutures through the tough tissue to form an array of sutures. Free ends of the sutures are extended out of the thoracic cavity and laid, spaced apart, on the patient's body. The free ends of the sutures are then individually threaded through an edge around the circumference of the replacement valve or a supporting cuff. Once all sutures have been run through the valve, all the sutures are pulled up taught and the valve is slid or "parachuted" down into place adjacent the tough tissue. Thereafter, the replacement valve is secured in place using the sutures.

Where replacement is performed utilizing an artificial valve, hand held instruments in the form of a stick can be affixed to the valve and used to manipulate the replacement valve into place. The commercially available replacement valves are typically provided with a detachable holder structure which can be engaged by the hand tools.

While the above described procedures are sufficient to successfully position a heart valve within the heart, they are particularly time consuming. A more stable platform would be desirable for maintaining the valve in a fixed position to allow it to by secured in place. Therefore, a need exists for apparatus and procedures of quickly and efficiently positioning and affixing artificial heart valves within the heart.

SUMMARY

Various embodiments of a prosthetic valve holder and valve holder assembly are provided. In a first preferred embodiment a prosthetic valve holder includes a first end portion for rigidly mounting to an articulating arm. The prosthetic valve holder releasably engages an attachment structure on a heart valve. A second end portion extends from the first end portion and preferably has at least two tines for capturing a portion of the attachment structure therebetween for use in valve replacement surgery.

An alternate preferred embodiment of the valve holder includes end portions that are coplanar. Another preferred embodiment has end portions that are offset on different parallel planes. A further preferred embodiment has one of the tines pivotally mounted on the other such that the tines are movable relative to each other so as to clamp the valve. Adjustments may be made to this embodiment by rotating a screw to adjust the angle between tines.

Still another preferred embodiment includes an extended portion disposed between the tines and attached at an intersection of the tines, the extended portion being offset from and parallel to the first end portion. This embodiment can also have the extended portion with a protrusion at a free end to capture the valve.

A method of surgery using the valve holder includes providing an articulating arm having a distalmost end. After attaching a valve holder to the distalmost end, the articulating arm is positioned over an operative site and a prosthetic valve is secured to the valve holder. The prosthetic valve is manipulated by the articulating arm to position the valve in a precise location. The valve is installed within an operative site in the heart by suturing, and the valve is detached from the holder.

In each of the above preferred embodiments and method, the proximal end of the articulating arm can be movably fixed to a frame, such as a stabilizing ring disposed about the operative site. Other instruments, such as retractors and other accessories can also be secured to the frame.

BRIEF DESCRIPTION OF THE DRAWINGS

Various preferred embodiments are described herein with reference to the drawings, wherein.

DETAILED DESCRIPTION OF PREFERRED EMBODIMENTS

Figure 1:
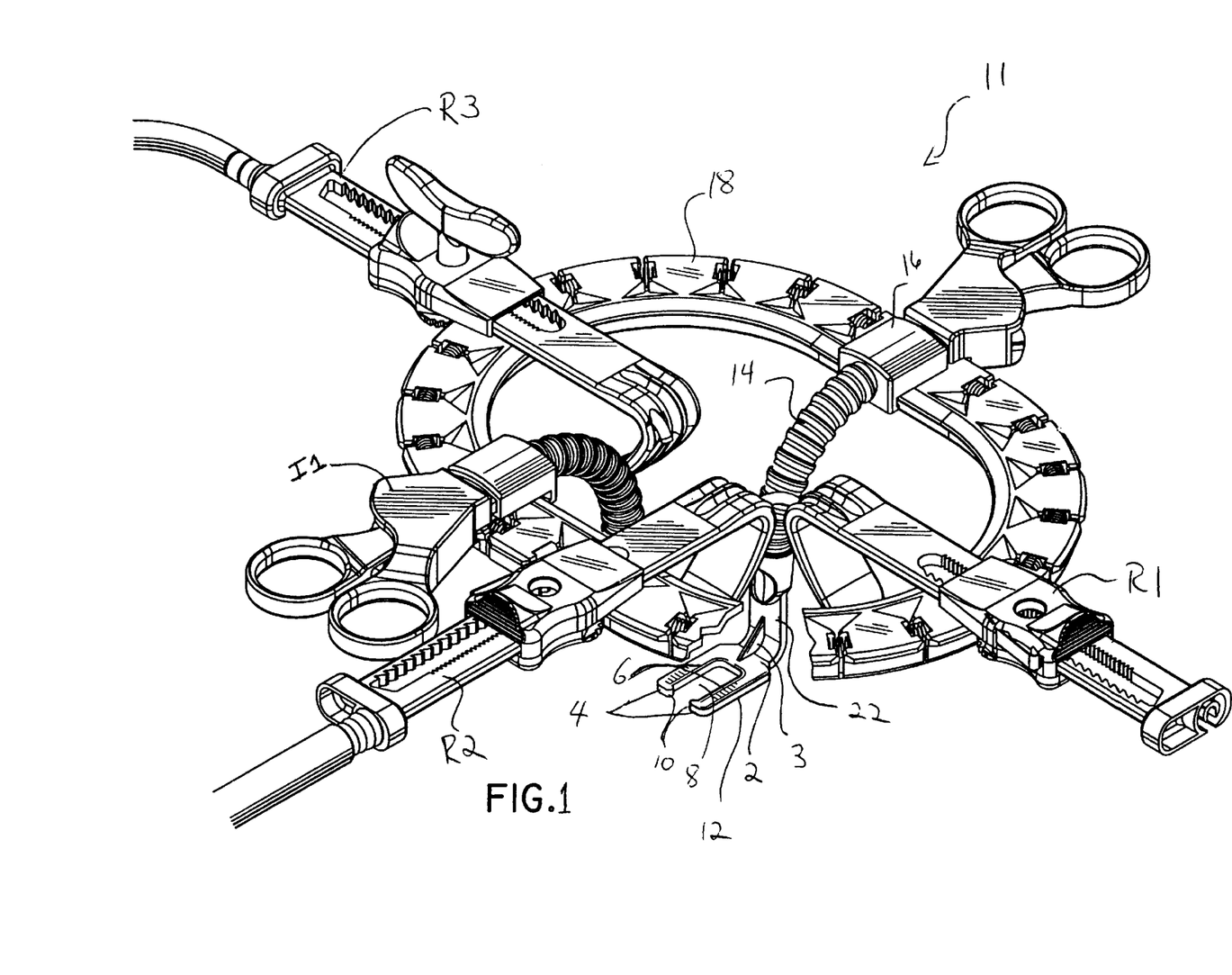
FIG. 1 shows an isometric view of a valve holder assembly mounted on a frame along with other instruments with a preferred embodiment valve holder attached to the distalmost end of an articulating arm.

Referring now in specific detail to the drawings in which like reference numerals identify similar or identical elements throughout the several views, and initially to FIG. 1, one preferred embodiment of a prosthetic valve holder constructed in accordance with the present disclosure is shown generally as valve holder 12. Valve holder 12 is provided for use with a valve holder assembly 11.

Valve holder assembly 11, generally includes a prosthetic valve holder 12, an articulating arm 14 and mounting assembly 16. Mounting assembly 16 is configured to allow articulating arm 14 to be movably secured to base 18. When secured, mounting assembly 16, articulating arm 14 and valve holder 12 can hold a prosthetic valve in a fixed position within the chest of a patient. Retractors R1, R2 and R3 can be used to hold back the tissue adjacent to the incision to allow the surgeon access to the heart. Other instruments can also be secured to base 18. Various retractors, bases and articulating instruments are commercially available from United States Surgical Corporation, Norwalk, Conn.

Figure 2:
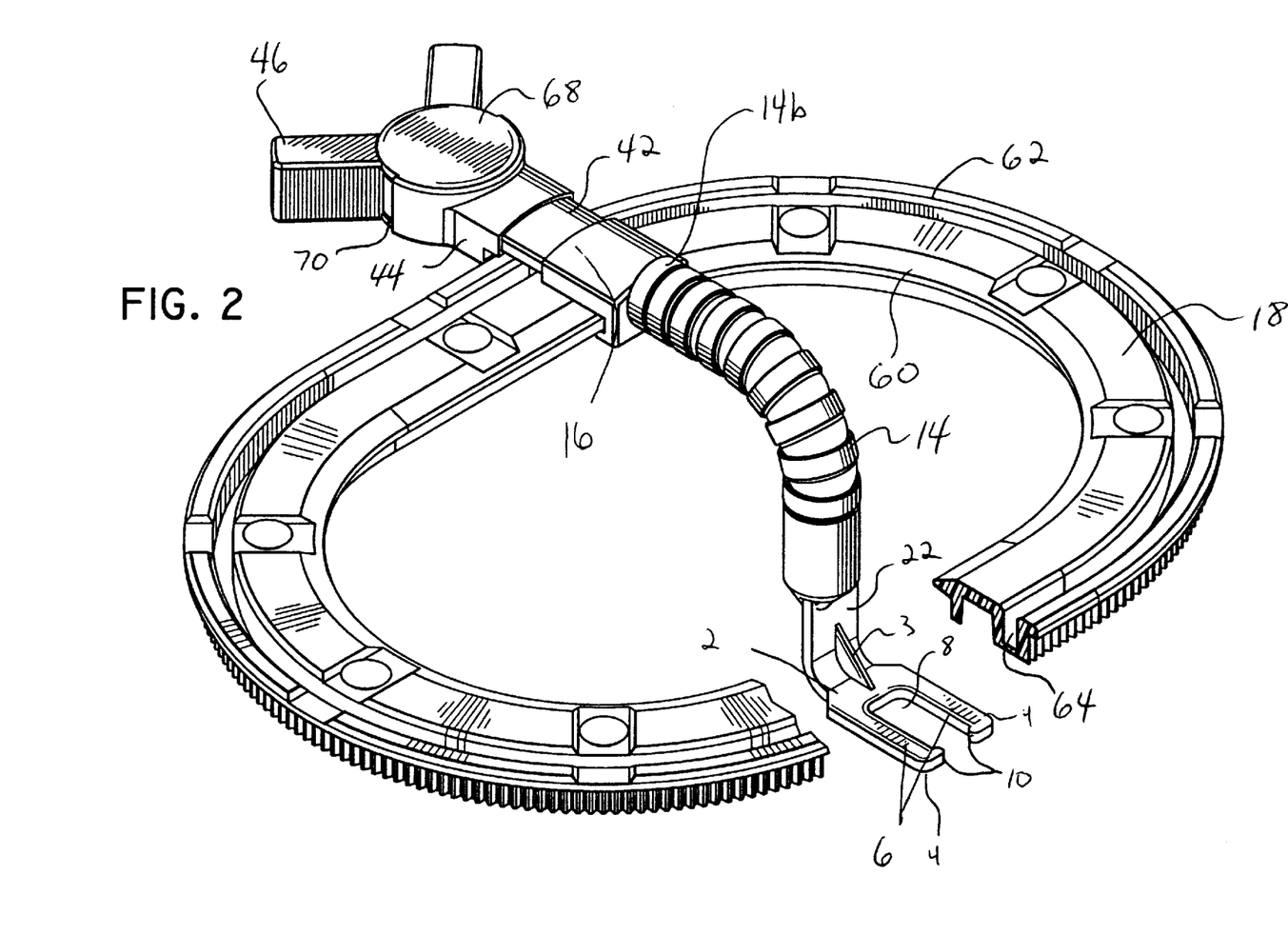
FIG. 2 is an isometric view of the valve holder assembly mounted on a frame.
Figure 4:
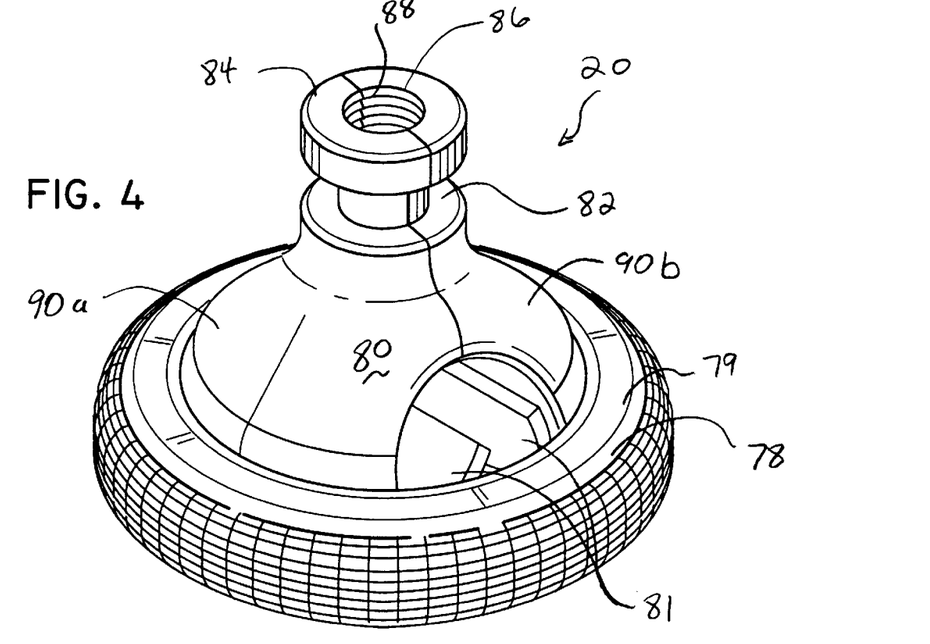
FIG. 4 is an isometric view of a heart valve with attachment structure.

Referring to FIGS. 1 and 2, a preferred embodiment of valve holder 12 includes a first end portion 2 and a second end portion 4. First end portion 2 is rigidly attached to a distalmost end 22 of articulating arm 14. Attachment can be achieved by snap fit, welding or other known techniques. A bracket support 3 is installed between distalmost end 22 of articulating arm 14 and first end portion 2. Second end portion 4 has a pair of tines 6 defining a gap 8 therebetween to receive groove portion 82 of valve 20 (FIG. 4). Tines 6 have opposing retaining bumps 10. Valve 20 is snapped in place by forcing it past retaining bumps 10. Once in position and sutured in place valve 20 can be unsnapped from tines 6 of valve holder 12 by passing it over the retaining bumps 10. Valve holder 12 can be made of a rigid sterilizable material preferably stainless steel, plastic or other suitable material.

Figure 3:
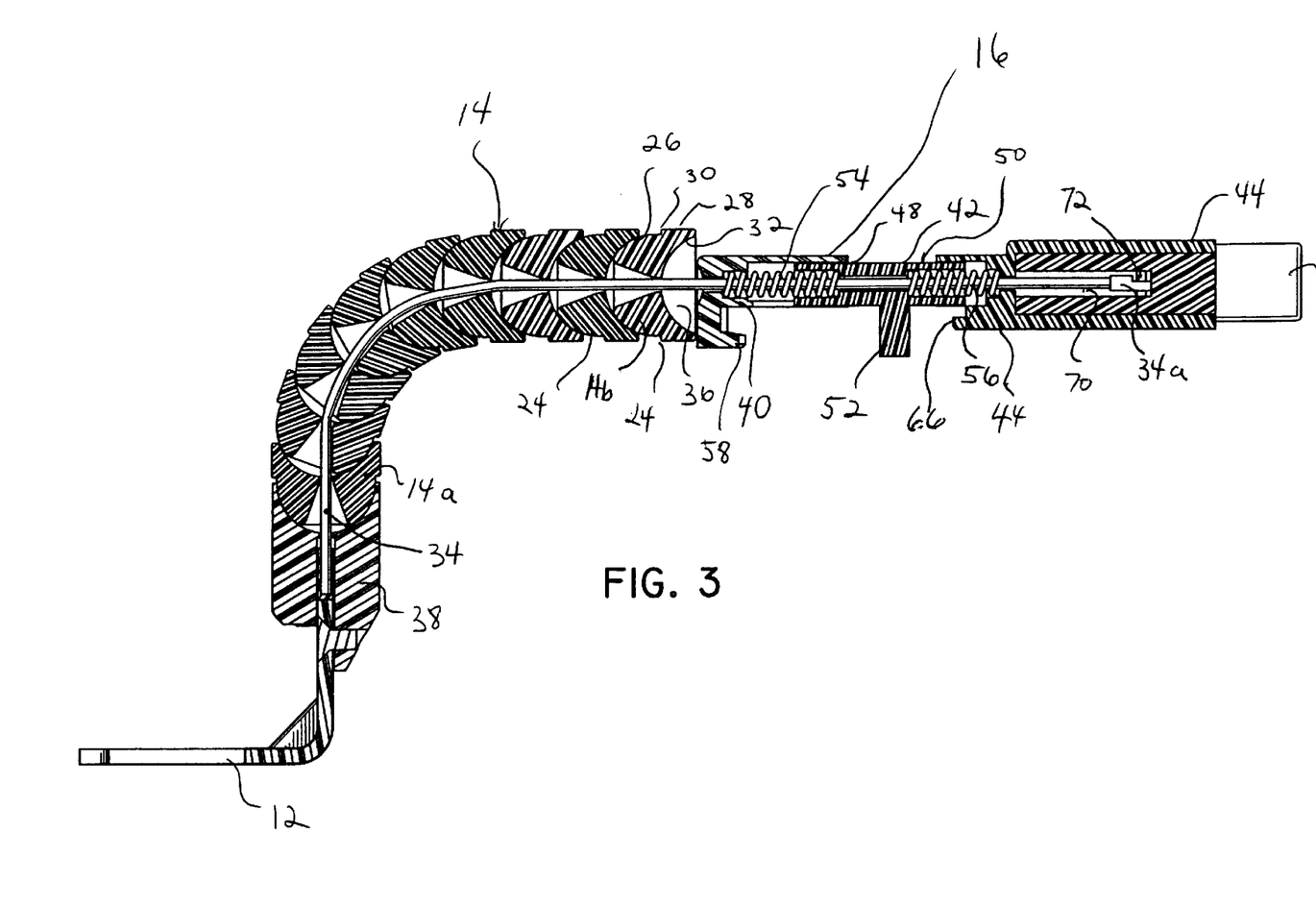
FIG. 3 is a cross sectional view of the valve holder and articulating arm.

Valve holder 12 is configured to releasably attach to a prosthetic heart valve 20. Valve holder is rigidly attached to distalmost end 22 of articulating arm 14. By mounting valve holder 12 on articulating arm 14, the position of valve holder can be precisely adjusted. As shown in FIG. 3, articulating arm 14 preferably consists of a plurality of link members 24 each of which has a hemispherical convex distal portion 26, a cylindrical body portion 28 including a peripheral step 30 and concave proximal end 32. Link members 24 are aligned such that convex distal portion 26 is received in concave proximal end 32 in a ball-and-socket type connection to permit a wide range of pivoting motion between adjoining link members 24. Link members 24 are concatenated by a cable 34 passing through each bore 36, and the distalmost link member 14a is fitted with an end portion 38 which mounts valve holder 12.

Mounting assembly 16 is mounted adjacent proximal most link member 14b and includes a mounting flange member 40, mounting base 42, toggle housing 44 and toggle 46. With reference to FIGS. 2 and 3, mounting base 42 has a flat bottom surface 48 to rest on a top surface 50 of base 42 and a peg 52 configured and dimensioned to be received in a groove 64 of base 18. Mounting flange member 40 and toggle housing 44 are slidably mounted with respect to mounting base by springs 54 and 56, respectively. Mounting flange member 40 has a flange 58 for engaging an inner rim 60 of base 18. Toggle housing 44 has a flange 66 for engaging an outer rim 62 of base 18.

Toggle 46 includes a cylindrical mounting portion 68 and toggle arm 70. See FIG. 3. Cylindrical mounting portion 68 is configured to be received within cylindrical recess 70 defined within toggle housing 44 and to be pivotably movable therein. Cable 34 extends through link members and through mounting flange member 40, spring 54, mounting 42, spring 56 and into cylindrical recess 70 of toggle housing 44. Proximal end portion 34a of cable 34 is pinned to toggle 46 by pin 72.

Figure 6:
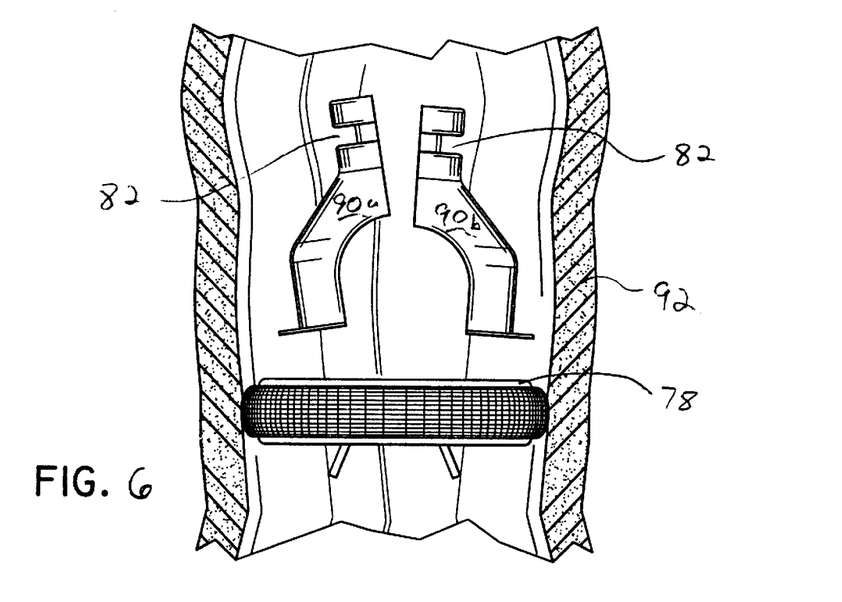
FIG. 6 shows a prosthetic heart valve placed within a patient's heart with an attachment portion disassembled.

Referring now to FIG. 4, a prosthetic valve 20 includes a valve portion 78 and an attachment portion 80. Attachment portion 80 defines a groove portion 82 thereabout further forming a flange 84 on the end portion 86 of valve portion 78. Attachment portion 80 is removably installed within an interior surface of valve portion 78. Attachment portion 80 defines a bore 86 having internal threads 88 disposed therein. Attachment portion 80 is formed of two halves 90a and 90b which are tied together with a suture (not shown) in the groove portion 82 to maintain attachment portion 80 structure and enable placement of valve portion 78. During heart valve replacement surgery the suture can be removed after installation of the valve 76 and two halves 90a and 90b are removable from a heart 92 as illustrated in FIG. 6. Valve portion 78 has a circular ring 79 with leaflets or flaps 81 pivotally mounted therein. Leaflets 81 open and close to allow blood flow and to restrict blood flow, respectively, during pumping cycles of the heart.

Figure 5:
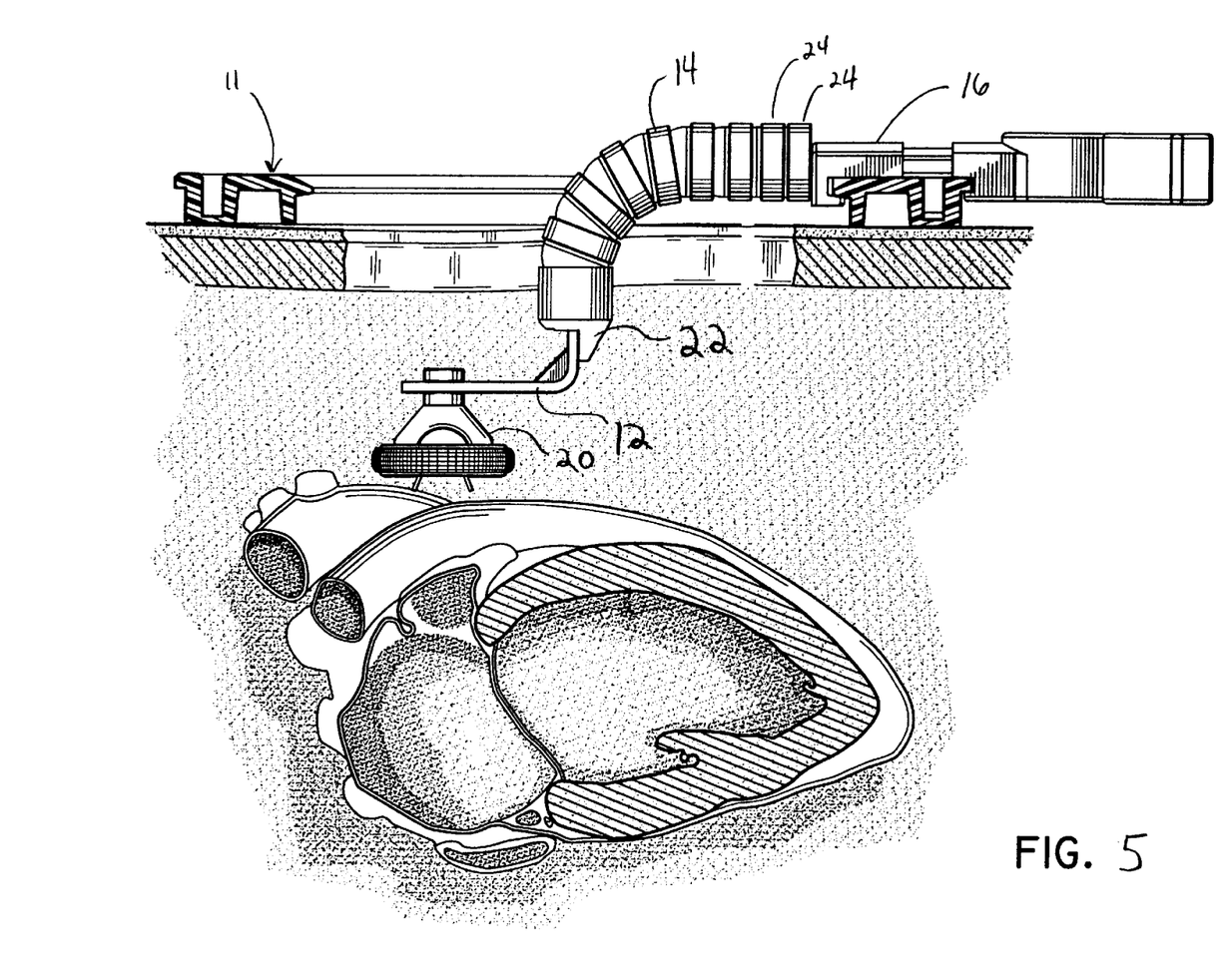
FIG. 5 shows a valve holder assembly with the attached heart valve being positioned in the thoracic cavity.

Referring now to FIG. 5, heart valve replacement surgery is performed to replace faulty or defect human valves. Replacement of valves requires access to the thoracic cavity and exposing the heart and blood vessels. The defective valve is cut away from the patient after the heart is sectioned and exposed. Valve 20 is positioned in place by attaching it to valve holder 12 which is attached to articulating arm 14. Articulating arm 14 is positioned to hold valve holder 12 and valve 20 within or above the heart walls. Once positioned, articulating arm 14 is locked in place using toggle 46 as described hereinabove. Valve 20 is then sutured, stapled or fastened by other means known in the art to the blood vessel walls. Valve holder 12 is unfastened from valve 20 and removed from the operative area. As shown in FIG. 6, the suture wrapped around groove portion 82 is cut allowing two halves 90a and 90b of attachment portion 80 to be unsecured from valve portion 78. Two halves 90a and 90b are removed from the operative area. The remaining tissue is sutured to valve portion 78 and the procedure is terminated as is known in the art.

Figures 7, 8:
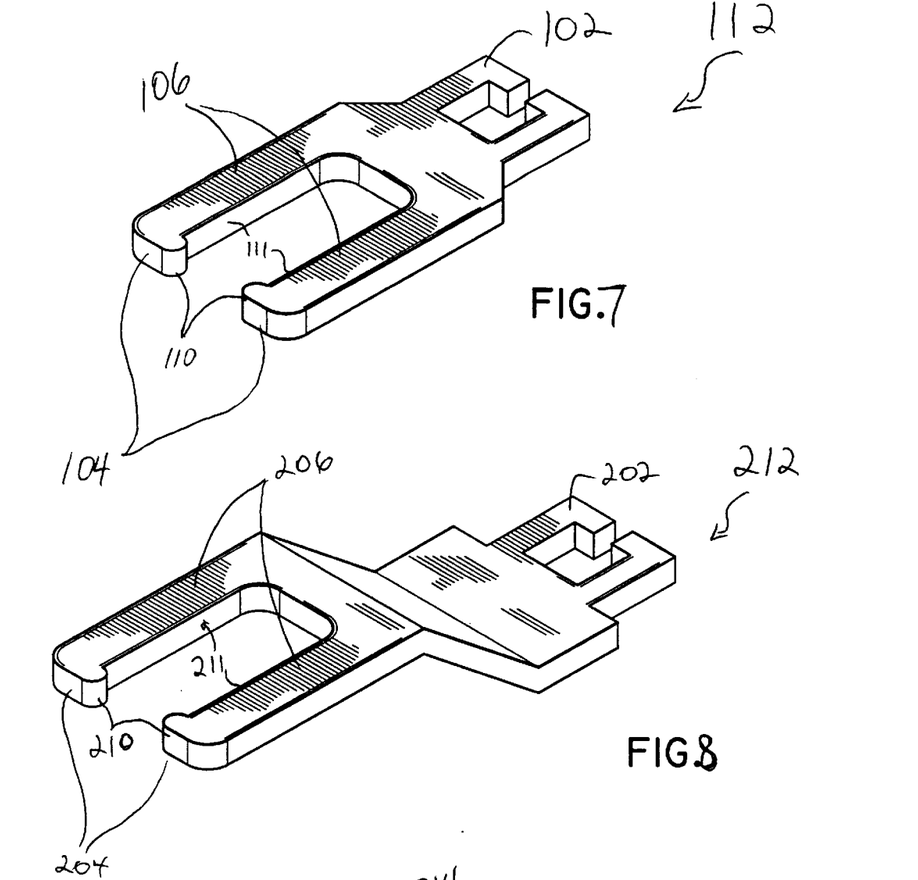
FIG. 7 shows an isometric view of an alternate embodiment of the heart valve holder.
FIG. 8 shows an isometric view of an alternate embodiment of a heart valve holder having an offset between end portions.

Referring to FIG. 7, an alternate embodiment of a prosthetic valve holder 112 includes a first end portion 102 and a second end portion 104 which is coplanar with first end portion 102. The first end portion 102 is adapted to receive distalmost end 22 of articulating arm 14. First end portion 102 is attached to distalmost end 22 by snap fitting into articulating arm 14. Second end portion 104 has a pair of tines 106 defining a gap 108 therebetween to receive groove portion 82 of valve 20. Tines 106 have opposing retaining bumps 110 on their interior sides 111. Valve 20 is snapped in place by forcing it past retaining bumps 110. Once in position and sutured in place valve 20 can be unsnapped from tines 106 of valve holder 12 by passing it over the retaining bumps 110.

In another alternate embodiment, as shown in FIG. 8, a second end portion 204 is offset from a first end portion 202 of a valve holder 212. First end portion 202 and second end portion 204 remain offset on parallel planes. The offset provides for additional valve clearance during operation. Retaining bumps 210 are provided on interior sides 211 of tines 206 to capture a valve, and first end portion 202 is adapted to receive the distalmost end of the articulating arm 14.

Figure 9:
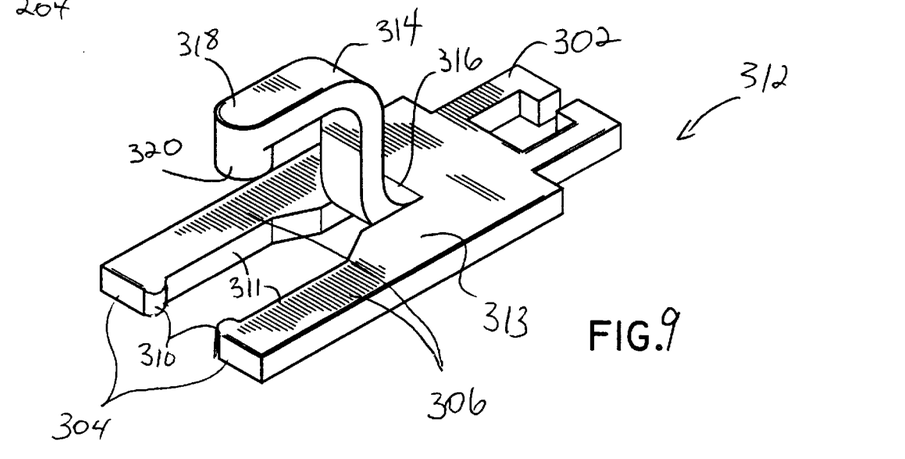
FIG. 9 shows an isometric view of an alternate embodiment of a heart valve holder having an extended portion.

Referring now to FIG. 9, a further embodiment of a valve holder 312 has a first end portion 302 to receive the distalmost end of articulating arm 14. A second end portion 304 includes tines 306 with retaining bumps 310 or interior sides 311, as before. Valve holder 312 includes an intermediate portion 313. Intermediate portion 313 has an extended portion 314 having an attached end portion 316 and a free end portion 318. Attached end portion 316 is rigidly coupled to intermediate portion 313 of valve holder 312. Free end portion 318 extends above and between tines 306 such that when a valve 20 is being held therebetween, extended portion 314 contacts attachment portion 80 of valve 20. Extended portion 314 provides a force against flange 84 of valve 20 to further secure valve 20. Free end portion 318 may have a protrusion 320 dimensioned and positioned to engage threaded bore 86 in the attachment portion 80 of valve 20.

Figure 10:
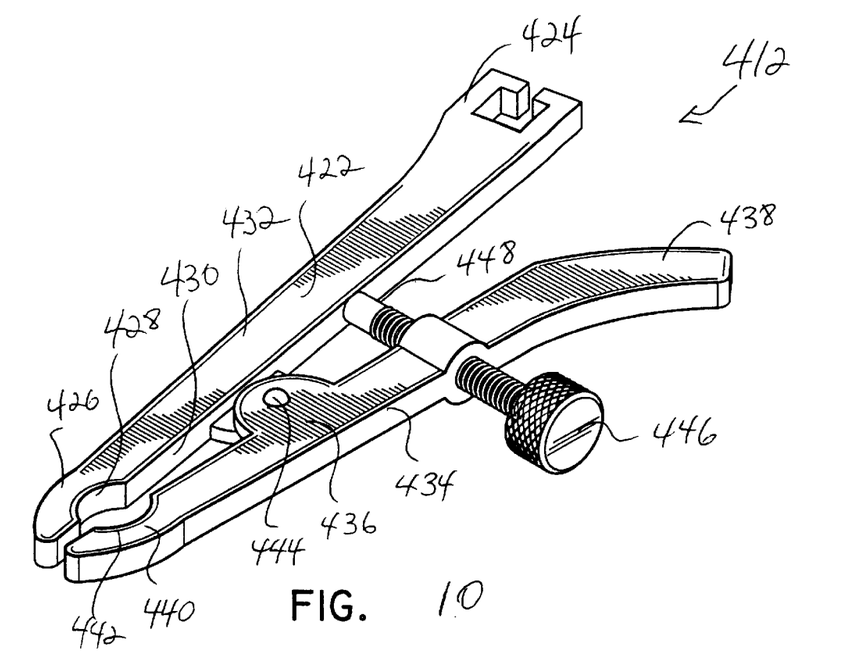
FIG. 10 shows an isometric view of an alternate embodiment of a heart valve holder having a first and second member pivotally attached.

Referring to FIG. 10, another embodiment of a prosthetic valve holder may be adjustable to accommodate various sized valves. Valve holder 412 includes a first member 422 having a first end portion 424 to receive the distalmost end of articulating arm 14. First member 422 has a second end portion 426 with an arcuate cut 428 on an interior side 430. In addition, first member 422 has an intermediate portion 432. A second member 434 includes an intermediate portion 436 pivotally connected to first member 422 at intermediate portion 432. Second member 434 has a first end portion 438 and a second end portion 440. Second end portion 440 has an arcuate shaped cut 442 therein which corresponds with and opposes arcuate shaped cut 428 of first member 422. Arcuate shaped cuts 426 and 442 receive groove portion 82 of valve 20 therebetween.

First member 422 and second member 434 pivot about their intermediate portions 432 and 436 for capturing and releasing valve 20. Pivot point 444 may have a biasing means, for example a torsion spring (not shown), to bias second end portions 426 and 440 of first member 422 and second member 434, respectively, into an opened release position. Alternately, first end portions 424 and 438 may have a thumb screw 446 or rachet mechanism (not shown) therebetween. Thumb screw 446 is rigidly mounted on first end portion 434. When thumb screw 446 is tightened, screw end 448 engages first end portion 424 of first member 422 drawing first end portions 424 and 438 apart and drawing second end portions 426 and 440 closer to hold valve 20 therebetween. When thumb screw 446 is loosened valve 20 is released. Thumb screw 446 or rachet (not shown) may be used in conjunction with a torsion spring (not shown) as described above.

Figure 11:
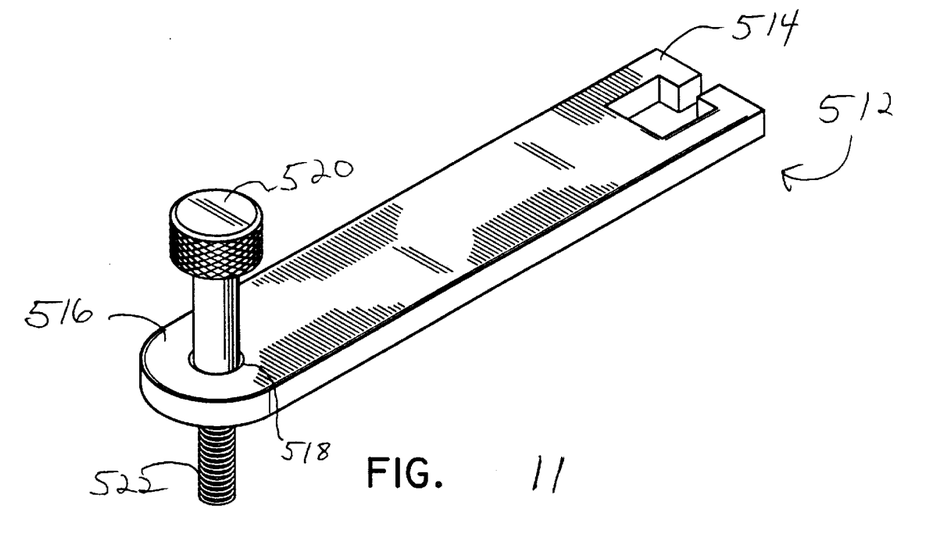
FIG. 11 shows an isometric view of an alternate embodiment of a heart valve holder having a screw to threadedly engage valve.

Referring to FIG. 11, in another alternate embodiment, a valve holder 512 includes a first end portion 514 and a second end portion 516. First end portion 514 is adapted to receive distalmost end 22 of the articulating arm 14. Second end portion 516 defines a bore 518 therethrough for receiving a thumb screw 520. Thumb screw 520 has a threaded end portion 522 which is passed through bore 518 and secured by a snap ring (not shown) within bore 518. This configuration allows thumb screw 520 to rotate within bore 518 without translation with respect to second end portion 516. Threaded end 522 engages threaded portion 88 of valve 20 and enables valve 20 to be released from valve holder 512 when the threads are disengaged during surgery.

It will be understood that various modifications may be made to the embodiments disclosed herein. For example, four or more tines may be used to secure the valve or tabs instead of bumps may be used. Also, various method steps and various orders of method steps can be derived from use of the disclosed instruments. Therefore, the above description should not be construed as limiting, but merely as exemplifications of preferred embodiments. Those skilled in the art will envision other modifications within the scope and spirit of the claims appended hereto.

What is claimed is:

1. A method of surgery comprising the steps of:
   providing an articulating arm having a distalmost end;
   attaching a valve holder to the distalmost end;
   positioning the articulating arm over an operative site;
   securing a prosthetic valve to the valve holder;
   installing the valve within a heart;
   detaching the valve from the valve holder; and
   wherein the step of securing a prosthetic valve to the valve holder includes:
      providing a pair of tines on the valve holder having opposing retaining bumps thereon; and
      snap fitting a groove on the prosthetic valve between the pair of tines on the valve holder.

2. A method of surgery comprising the steps of:
   providing an articulating arm having a distalmost end;
   attaching a valve holder to the distalmost end;
   positioning the articulating arm over an operative site;
   securing a prosthetic valve to the valve holder;
   installing the valve within a heart;
   detaching the valve from the valve holder; and
   wherein the step of securing a prosthetic valve to the valve holder includes:
      providing a pair of pivotally connected tines;
      providing means for securing the pair of tines with a relative displacement therebetween; and
      fitting a groove on the prosthetic valve between the pair of tines on the valve holder.

3. A method of surgery comprising the steps of:
   providing an articulating arm having a distalmost end;
   attaching a valve holder to the distalmost end;
   positioning the articulating arm over an operative site;
   securing a prosthetic valve to the valve holder;
   installing the valve within a heart;
   detaching the valve from the valve holder; and
   wherein the step of securing a prosthetic valve to the valve holder includes:

providing a threaded portion on the prosthetic valve; and engaging the threaded portion with a thumb screw mounted on the valve holder.

4. A method of surgery comprising the steps of:

providing an articulating arm having a distalmost end;

attaching a valve holder to the distalmost end;

positioning the articulating arm over an operative site;

securing a prosthetic valve to the valve holder;

installing the valve within a heart;

detaching the valve from the valve holder; and wherein the step of securing a prosthetic valve to the valve holder includes:

providing a pair of tines having opposing retaining bumps thereon;

providing an extended portion disposed between the tines and attached at an intersection of the tines, the extended portion being off-set from and parallel to the first end portion; and snap fitting a groove on the prosthetic valve between the pair of tines and the extended portion on the valve holder.

* * * * *